(12) United States Patent
Nagao et al.

(10) Patent No.: US 8,759,588 B2
(45) Date of Patent: Jun. 24, 2014

(54) PROCESS FOR PRODUCING XYLYLENEDIAMINE

(75) Inventors: Shinichi Nagao, Okayama (JP); Tatsuyuki Kumano, Okayama (JP); Kenji Nakaya, Okayama (JP); Ryusuke Shigematsu, Okayama (JP); Kinji Kato, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 302 days.

(21) Appl. No.: 13/062,334

(22) PCT Filed: Aug. 27, 2009

(86) PCT No.: PCT/JP2009/064989
§ 371 (c)(1),
(2), (4) Date: Jun. 17, 2011

(87) PCT Pub. No.: WO2010/026920
PCT Pub. Date: Mar. 11, 2010

(65) Prior Publication Data
US 2011/0245540 A1 Oct. 6, 2011

(30) Foreign Application Priority Data
Sep. 8, 2008 (JP) .................................. 2008-230164

(51) Int. Cl.
*C07C 209/00* (2006.01)

(52) U.S. Cl.
USPC ........................................................ 564/415

(58) Field of Classification Search
None
See application file for complete search history.

(56) References Cited

U.S. PATENT DOCUMENTS

| | | | |
|---|---|---|---|
| 2,970,170 A * | 1/1961 | Lind | ............................. 564/385 |
| 5,817,589 A | 10/1998 | De Agudelo et al. | |
| 5,877,364 A | 3/1999 | Hernandez et al. | |
| 6,905,997 B2 | 6/2005 | Ohlbach et al. | |
| 2002/0177735 A1 | 11/2002 | Kanamori et al. | |
| 2008/0154061 A1 | 6/2008 | Ernst et al. | |
| 2009/0048466 A1* | 2/2009 | Lettmann et al. | ............. 564/448 |
| 2009/0149314 A1 | 6/2009 | Ernst et al. | |
| 2010/0168474 A1 | 7/2010 | Kumano et al. | |

FOREIGN PATENT DOCUMENTS

| | | | |
|---|---|---|---|
| DE | 102006006625 | * 8/2007 | ............. C07B 43/04 |
| JP | 9 271675 | 10/1997 | |
| JP | 2003 38956 | 2/2003 | |
| JP | 2003 38958 | 2/2003 | |
| JP | 2004 508928 | 3/2004 | |
| JP | 2007 104663 | 9/2007 | |
| JP | 2008 531521 | 8/2008 | |

OTHER PUBLICATIONS

International Search Report Issued Sep. 29, 2009 in PCT/JP09/064989 filed Aug. 27, 2009.

* cited by examiner

*Primary Examiner* — Clinton Brooks
(74) *Attorney, Agent, or Firm* — Oblon, Spivak, McClelland, Maier & Neustadt, L.L.P.

(57) ABSTRACT

The invention provides a process for producing xylylenediamine, including supplying a solution of phthalonitrile dissolved in a solvent to a reactor filled with a catalyst and hydrogenating the phthalonitrile to produce xylylenediamine, characterized in that the process includes halting supply of the solution; (2) bringing a washing liquid into contact with the catalyst, the washing liquid having a phthalonitrile content of 3 mass % or less and a xylylenediamine content of 1 mass % or more; and after completion of the contact, resuming supply of the solution, and employing the catalyst continuously in hydrogenation. Through the production process of the invention, the catalyst can be employed continuously for a long period of time, and the catalyst-related cost can be considerably reduced.

17 Claims, No Drawings

PROCESS FOR PRODUCING XYLYLENEDIAMINE

This application is a 371 of PCT/JP09/64989 filed Aug. 27, 2009. Priority to Japanese patent application 2008-230164 filed Sep. 8, 2008, is claimed.

TECHNICAL FIELD

The present invention relates to a process for producing xylylenediamine, which process comprises performing catalytic hydrogenation (hereinafter may be abbreviated as simply "hydrogenation") of phthalonitrile by means of a reactor filled with a catalytic hydrogenation catalyst (hereinafter may be referred to as "hydrogenation catalyst," "catalyst," or "catalyst layer").

BACKGROUND ART

There have already been known processes for producing xylylenediamine, which include hydrogenating phthalonitrile through a flow method employing a heterogeneous catalyst (i.e., trickle-bed mode).

One disclosed process is continuous catalytic hydrogenation through the fixed-bed method, in which phthalonitrile is reduced through catalytic hydrogenation under liquid-gas-solid tri-phase conditions in the presence of a heterogeneous nickel-copper-molybdenum catalyst (see Patent Document 1).

In the process for producing xylylenediamine which includes hydrogenating phthalonitrile in the presence of a heterogeneous catalyst through the fixed-bed method, the activity of the hydrogenation catalyst, which is a heterogeneous catalyst, is deteriorated rapidly, which is problematic. Therefore, when hydrogenation of phthalonitrile is performed for a long time through the fixed-bed method, the hydrogenation catalyst must be regenerated and activated.

Generally, in industrial production, the catalyst is required to have a catalyst life of at least one year. The catalytic performance such as catalytic activity is conceivably impaired, because of complicated factors. In the case of the hydrogenation catalyst employed in hydrogenation of phthalonitrile to produce xylylenediamine, the drop in catalytic activity is attributable to a plurality of factors. One conceivable factor is deposition on a catalyst surface of high-boiling-point organic by-products formed through polymerization or condensation. As used herein, the term "catalyst life" refers not to the period of time until the catalyst no longer exhibits catalytic activity, but to the period of time during which the catalyst can be continuously employed in industrial production.

The process for producing xylylenediamine through hydrogenation of phthalonitrile in the presence of a heterogeneous catalyst in the fixed-bed mode has a problem in that, in addition to a drop in catalytic activity, high-boiling-point by-products plug a part of the catalyst layer, to thereby increase inner pressure loss of the reactor (differential pressure in the catalyst layer), failing to supply phthalonitrile solution serving as a raw material and impeding continuous operation. Since continuous operation is impeded by deposition of high-boiling-point by-products on the catalyst layer, the high-boiling-point by-products deposited on the catalyst layer must be removed.

In conventional processes for producing xylylenediamine, one known means for regenerating and activating the catalyst is hydrocracking. In one specific procedure, the catalytic hydrogenation catalyst which has been employed in hydrogenation of dicyanobenzene (i.e., phthalonitrile) and which exhibits lowered catalytic activity is brought into contact with hydrogen-containing gas at 200 to 500° C., and the rate of heating the catalytic hydrogenation catalyst is controlled to 40° C./min or less during the contact of the catalyst with hydrogen-containing gas, whereby the catalyst is regenerated, and the differential pressure of the catalyst layer is improved. The thus-regenerated catalyst is reused in hydrogenation of dicyanobenzene (see Patent Document 2).

PRIOR ART DOCUMENTS

Patent Documents

Patent Document 1: Japanese patent Publication (kokoku) No. Sho 53-20969
Patent Document 2: Japanese Patent Application Laid-Open (kokai) No. 2004-107327

SUMMARY OF THE INVENTION

Problems to be Solved by the Invention

The method disclosed in Patent Document 2 involving subjecting the catalyst to hydrocracking requires very complex, cumbersome operations of hydrocracking. In addition, an additional apparatus for heating the gas employed in hydrocracking must be provided, and sintering and pulverization of the catalyst may readily occur due to high-temperature treatment. Thus, there has been demand for an alternative method for hydrocracking.

Under such circumstances, an object of the present invention is to provide a process for producing xylylenediamine including hydrogenating phthalonitrile, in which the hydrogenation catalyst employed in hydrogenation which exhibits reduced catalytic activity or which has increased the differential pressure of the catalyst layer is regenerated or activated, and the differential pressure of the catalyst layer is improved, so as to ensure continuous use of the catalyst.

Means for Solving the Problems

The present inventors have conducted extensive studies, and have found that the aforementioned object can be attained by halting supply of a solution of phthalonitrile dissolved in a solvent and, in this state, bringing a washing liquid into contact with the catalyst, the washing liquid having a phthalonitrile content of 3 mass % or less and a xylylenediamine content of 1 mass % or more. The present invention has been accomplished on the basis of this finding.

Accordingly, the present invention is directed to a process for producing xylylenediamine as described in any one of the following [A] to [H].

[A] A process for producing xylylenediamine, including supplying a solution of phthalonitrile dissolved in a solvent to a reactor filled with a catalyst and hydrogenating the phthalonitrile to produce xylylenediamine, characterized in that the process comprises:
  (1) halting supply of the solution;
  (2) bringing a washing liquid into contact with the catalyst, the washing liquid having a phthalonitrile content of 3 mass % or less and a xylylenediamine content of 1 mass % or more; and
  (3) after completion of the contact, resuming supply of the solution, and employing the catalyst continuously in hydrogenation.

[B] The process for producing xylylenediamine as described in [A] above, wherein, in (2) above, the washing liquid is brought into contact with the catalyst at 20 to 180° C.
[C] The process for producing xylylenediamine as described in [A] or [B] above, wherein the washing liquid employed in (2) is a hydrogenation reaction mixture obtained through hydrogenation of phthalonitrile.
[D] The process for producing xylylenediamine as described in any one of [A] to [C] above, wherein, in (2) above, at least a portion of the washing liquid is brought into contact with the catalyst in a circulation flow mode or a one-path flow mode.
[E] The process for producing xylylenediamine as described in any one of [A] to [D] above, wherein, in (2) above, the washing liquid is brought into contact with the catalyst under hydrogen and/or nitrogen.
[F] The process for producing xylylenediamine as described in any one of [A] to [E] above, wherein the phthalonitrile is isophthalonitrile.
[G] The process for producing xylylenediamine as described in any one of [A] to [F] above, wherein the solvent is liquid ammonia.
[H] The process for producing xylylenediamine as described in any one of [C] to [F] above, wherein the solvent is liquid ammonia, and a hydrogenation reaction mixture from which a portion or the entirety of the liquid ammonia has been removed is employed as the washing liquid in (2) above.

Effects of the Invention

According to the present invention, in the production of xylylenediamine by hydrogenating phthalonitrile, the activity of the catalyst lowered during hydrogenation can be restored. In the case of the fixed-bed method, the differential pressure generated in the catalyst layer is improved to thereby regenerate the catalyst to an employable level, whereby the catalyst can be continuously employed as a phthalonitrile hydrogenation catalyst.

According to the invention, a washing liquid having a phthalonitrile content of 3 mass % or less and a xylylenediamine content of 1 mass % or more (hereinafter may be referred to simply as "washing liquid") is brought into contact with the hydrogenation catalyst whose catalytic activity has been lowered during hydrogenation in a circulation flow mode or a one-path flow mode, whereby the catalyst is cleaned. Since this cleaning operation is very easily performed, the catalyst can be readily cleaned while it is installed in the reactor. Thus, the present invention is industrially useful.

Further, according to the present invention, the catalyst can be regenerated at lower temperature as compared with hydro-cracking disclosed in, for example, Patent Document 2. Therefore, there can be avoided both an uncontrollable state of the reactor which would otherwise be caused by sudden rise of the catalyst temperature, and deterioration of the catalyst (e.g., sintering or pulverization), and the catalyst can be effectively regenerated in a safe manner. As a result, the catalyst can be employed continuously for a long period of time, and the catalyst-related cost can be considerably reduced.

MODES FOR CARRYING OUT THE INVENTION

Phthalonitrile

Examples of the phthalonitrile serving as a raw material (hereinafter may be referred to as raw phthalonitrile) employed in the present invention include orthophthalonitrile, isophthalonitrile, and terephthalonitrile. In the present invention, these phthalonitriles may be used singly or in combination of two or more species.

In the production process of the present invention, isophthalonitrile is preferably employed as a raw material. The isophthalonitrile may be a mixture thereof having a orthophthalonitrile content or a terephthalonitrile content of preferably 10 mass % or less, with respect to total amount of all phthalonitrile species (more preferably 6 mass % or less).

Examples of the method for producing phthalonitrile include ammoxidation of alkyl-substituted benzene such as xylene; reaction between dichlorobenzene with hydrogen cyanide; and reaction between phthalic acid with ammonia. In the industry, ammoxidation of alkyl-substituted benzene such as xylene is generally employed.

Specifically, ammoxidation of xylene may be performed through a known method in the presence of a known catalyst, as disclosed in, for example, Japanese patent Publication (kokoku) No. Sho 49-45860, Japanese Patent Application Laid-Open (kokai) Nos. Sho 49-13141, Sho 63-190646, Hei 5-170724, Hei 1-275551, Hei 5-170724, and Hei 9-71561.

<Process for Producing Xylylenediamine>

In the present invention, a phthalonitrile is dissolved in a solvent, and the solution is supplied to a reactor filled with a catalyst for hydrogenation, to thereby yield a xylylenediamine.

The xylylenediamine produced through the production process of the present invention includes three isomers: o-xylylenediamine, m-xylylenediamine, and p-xylylenediamine. When isophthalonitrile is employed as a raw material, m-xylylenediamine is a main product.

Phthalonitrile may be hydrogenated through the method disclosed in Patent Document 1. In one specific embodiment, a heterogeneous catalyst is charged into a reactor, and a phthalonitrile solution prepared through dissolving a phthalonitrile in a solvent is supplied to a reactor with hydrogen (i.e., trickle-bed mode). In the trickle-bed mode, phthalonitrile is catalytically and continuously reduced through hydrogenation in the presence of a heterogeneous catalyst under gas-liquid-solid tri-phase conditions. In the case where continuous catalytic hydrogenation through the trickle-mode method employing a heterogeneous catalyst is performed, the effects of regeneration and activation of the catalyst attributed to the below-mentioned catalyst washing operation can be fully attained.

In the present invention, no particular limitation is imposed on the reaction mode of hydrogenation of phthalonitrile, and the fixed-bed mode or the suspension bed mode may be employed. Of these, the fixed bed is preferred. The hydrogenation is performed by means of a reactor of a continuous flow type.

The heterogeneous catalyst in the fixed bed may be a known catalyst such as a metal-on-carrier catalyst, a carrier-less metal catalyst, a Raney catalyst, or a noble metal catalyst. Examples of preferred metals of the catalyst include nickel, cobalt, and palladium. The metal content of the catalyst is preferably 10 to 95 mass %, more preferably 20 to 80 mass %, still more preferably 30 to 70 mass %. The carrier is preferably diatomaceous earth, silica, alumina, silica-alumina, magnesia, zirconia, titania, or activated carbon.

Hydrogenation of phthalonitrile is preferably performed at a reaction temperature of 20 to 200° C., more preferably 30 to 160° C., still more preferably 40 to 120° C. Hydrogenation of phthalonitrile is preferably performed at a reaction pressure (hydrogen pressure) of 1 to 30 MPa, more preferably 2 to 20 MPa, still more preferably 3 to 15 MPa.

The solvent for dissolving raw-material phthalonitrile may be selected from among liquid ammonia and a variety of solvents which are stable under hydrogenation conditions. Specific examples of the solvent other than liquid ammonia include aromatic hydrocarbon solvents such as toluene, xylene, and trimethylbenzene; ether solvents such as tetrahydrofuran and dioxane; alcohol solvents such as methanol, ethanol, and propanol; and aromatic monoamine solvents such as benzylamine and methylbenzylamine. Among these solvents, liquid ammonia and aromatic hydrocarbon solvents are preferred, with liquid ammonia being more preferred.

(Catalyst Washing Operation)

When hydrogenation of phthalonitrile is continuously performed for a long period of time in the presence of the same catalyst, the activity of the catalyst decreases, and the differential pressure of the catalyst layer increases. In this case, continuous production of xylylenediamine is impeded.

Thus, according to the present invention, the following operations (1) to (3) are performed, whereby sintering and pulverization of the catalyst can be prevented; the catalyst can be effectively regenerated and activated; and the differential pressure of the catalyst layer can be reduced. The operations are as follows:

(1) halting supply of the solution of phthalonitrile as a raw material;
(2) bringing a washing liquid into contact with the catalyst, the washing liquid having a phthalonitrile content of 3 mass % or less and a xylylenediamine content of 1 mass % or more; and
(3) after completion of the contact, resuming supply of the solution, and employing the catalyst continuously in hydrogenation.

There are some conceivable causes for deactivation of the catalyst employed in hydrogenation. Conceivably, the catalyst undergoes deactivation or permanent poisoning by sintering of catalytic active ingredients due to a thermal load; migration of an ingredient which may serve as a catalyst poison to an active ingredient and/or a catalyst ingredient; or other causes.

Notably, the term "deactivation" does not necessarily refer to complete loss of catalytic function in the target hydrogenation, but to an industrially unuseful state from the viewpoints of productivity, utility, cost, etc.

—Operation (1)—

As the catalytic activity decreases, the 3-cyanobenzylamine serving as a reaction intermediate (hereinafter referred to as reaction intermediate CBA) of the reaction mixture increases. Thus, in continuation of hydrogenation, the differential pressure of the hydrogenation catalyst increases. In (1) above, the timing of halting the supply of a solution of raw-material phthalonitrile may be determined on the basis of the reaction intermediate CBA concentration or the differential pressure of the catalyst layer, serving as an index.

More specifically, when the reaction intermediate CBA concentration has reached preferably 13 mass % or higher, more preferably 10 mass % or higher, still more preferably 6 mass % or higher, the supply of a solution of raw-material phthalonitrile may be halted. Alternatively, when an increase in differential pressure of the catalyst layer has just been observed, the supply of a solution of raw-material phthalonitrile may be halted. In order to realize reliable production of xylylenediamine, the supply of a solution of raw-material phthalonitrile is preferably halted before the failure of the supply of a solution of raw-material phthalonitrile. The differential pressure of the catalyst layer is a value calculated through the procedure described in the Examples.

Yet alternatively, instead of employing the reaction intermediate CBA concentration or the differential pressure of the catalyst layer as an index, it is effective to halt the supply at such specific intervals that the catalytic activity is not excessively lowered and the differential pressure of the catalyst layer is not excessively increased.

—Operation (2)—

After halting of the supply of a solution of raw-material phthalonitrile, a washing liquid is fed to a reactor filled with a catalyst, so as to bring the washing liquid into contact with the catalyst. Through performing operation (2), the catalyst can be regenerated and activated, and the differential pressure of the catalyst layer can be improved. One conceivable for this is that an organic substance which is under transformation to high-boiling-point by-products via polymerization, condensation, etc. (hereinafter referred to as high-boiling-point by-product precursor) is successfully removed from the catalyst surface.

In other words, during operation (1) above, the supply of a solution of raw-material phthalonitrile is preferably halted at the point in time when no substantial increase in reaction intermediate CBA or differential pressure of the catalyst layer is observed, so as to fully attain the effect of operation (2). When deactivation of the catalyst is mainly attributed to a decrease in number of active sites (i.e., hydrogenation spots) caused by adsorption of the aforementioned high-boiling-point by-product precursor on the catalyst surface, the catalytic activity can be restored through removal of the adsorbed high-boiling-point by-product precursor adsorbed from the catalyst surface.

The washing liquid employed in operation (2) has a phthalonitrile content of 3 mass % or less, and a xylylenediamine content of 1 mass % or more.

For regenerating and activating the catalyst and reducing the differential pressure of the catalyst layer, the xylylenediamine content of the washing liquid is essentially 1 to 100 mass %, preferably 3 to 100 mass %, more preferably 5 to 100 mass %, still more preferably 10 to 100 mass %, yet more preferably 50 to 100 mass %, yet more preferably 90 to 100 mass %, yet more preferably 95 to 100 mass %, further more preferably 99 to 100 mass %.

In the case where the target reaction product is m-xylylenediamine, m-xylylenediamine (i.e., the target reaction product) may be used as a washing liquid. Regarding other isomers, similarly, o-xylylenediamine or p-xylylenediamine (i.e., the target reaction product) may be used as a washing liquid in the case where the target reaction product is o-xylylenediamine or p-xylylenediamine.

Note that when the target reaction product is m-xylylenediamine, an m-xylylenediamine (i.e., the target reaction product) washing liquid containing another isomer (o-xylylenediamine or p-xylylenediamine) may also be used. However, when such a mixed isomer washing liquid is used, an optional operation and apparatus for separating and collecting an unnecessary isomer through distillation are needed.

Meanwhile, for regenerating and activating the catalyst and reducing the differential pressure of the catalyst layer, the raw-material phthalonitrile content of the washing liquid is essentially 3 mass % or less, preferably 1 mass % or less, more preferably 0.1 mass % or less, still more preferably 0.005 mass % or less. In some cases, industrially available xylylenediamine and the xylylenediamine yielded through the production process of the present invention may contain raw-material phthalonitrile. Therefore, if needed, the phthalonitrile content must be adjusted to fall within the above range before use.

In the process for producing xylylenediamine including hydrogenation of a solution raw-material phthalonitrile dissolved in a solvent in the presence of a heterogeneous catalyst, the phthalonitrile content of the hydrogenation reaction mixture which has passed through the reaction zone (catalyst layer) of the reactor is appropriately adjusted to fall within the above range before use as the washing liquid. This simple procedure is particularly preferred in industrial production. The hydrogenation reaction mixture from which a portion or the entirety of the solvent (e.g., liquid ammonia) has been removed may be employed as the washing liquid.

Notably, when the hydrogenation reaction mixture is used as the washing liquid as described above, the reaction intermediate CBA concentration and the high-boiling-point by-product (including high-boiling-point by-product precursor) concentration of the washing liquid are preferably 10 mass % or less, more preferably 5 mass % or less, still more preferably 2 mass % or less, particularly preferably substantially 0 mass %, for satisfactorily washing the catalyst.

When the washing liquid has high viscosity, the viscosity may be lowered by adding to the washing liquid a solvent for dissolving raw-material phthalonitrile. The solvent for reducing the viscosity is preferably liquid ammonia or an aromatic hydrocarbon solvent, with liquid ammonia being more preferred.

The temperature at which the washing (contacting) is performed in operation (2) may be selected from a wide range. So long as the liquid phase can be maintained at a given pressure, a higher temperature is more effective. However, since the solvent or other materials may be thermally degraded at excessively high temperature, the washing temperature is a temperature approximating generally employed hydrogenation temperature. Specifically, the washing temperature is preferably 20 to 180° C., more preferably 40 to 140° C., still more preferably 60 to 120° C., yet more preferably 60 to 110° C.

The washing (contacting) time is 30 minutes or longer, more preferably 1 to 20 hours, for regenerating and activating the catalyst and reducing the differential pressure of the catalyst layer.

Through bringing the washing liquid into contact with the catalyst (i.e., washing the catalyst), at least a part of raw-material phthalonitrile, reaction products, high-boiling-point by-products (polymer, condensate, etc.), high-boiling-point by-product precursors, etc. which have been adsorbed on the catalyst are conceivably removed.

When the temperature at the contact between the catalyst and the washing liquid is maintained to fall within the aforementioned range while the pressure inside the reactor before halting reaction is maintained; or when the temperature of the washing liquid is maintained to fall within the above range, washing is performed, whereby the high-boiling-point by-product precursor can be dissolved in a larger amount in the washing liquid, resulting in high washing efficiency.

In order to resume hydrogenation immediately after completion of washing, the pressure inside the reactor during washing of the catalyst is preferably 1 to 30 MPa, more preferably 3 to 20 MPa, still more preferably 3 to 15 MPa.

The operation of bringing the washing liquid into contact with the catalyst may be performed under hydrogen and/or nitrogen.

No particular limitation is imposed on the operation of bringing the washing liquid into contact with the catalyst. In one embodiment of the operation, supplying of the raw-material phthalonitrile solution is halted, and then the reactor is filled with the washing liquid, to thereby bring the washing liquid into contact with the catalyst. In another embodiment of the operation, at least a portion of the washing liquid is caused to flow through the reactor in a circulation flow mode or a one-path flow mode, to thereby bring the washing liquid into contact with the catalyst.

As used herein, the circulation flow mode refers to a flow mode in which at least a portion of the washing liquid is circulated from the outlet of a continuous-flow reactor to the inlet of the reactor. The one-path flow mode refers to a flow mode in which the washing liquid discharged through the outlet of a continuous-flow reactor is not reused.

In operation (2), the conditions: temperature, pressure, time, and amount of washing liquid, are not fixed. During the operation, at least one condition may be modified, to thereby tune at least one other condition.

Similarly, the gas flow rate of hydrogen and nitrogen employed in washing operation for forming a trickle flow, the hydrogen concentration, etc. are not fixed.

During the operation, at least one condition may be modified, to thereby tune at least one other condition.

—Operation (3)—

Alternatively, after completion of operation (2), supply of the raw-material phthalonitrile solution is resumed, and hydrogenation of phthalonitrile is resumed in the presence of the catalyst which has undergone the washing operation. Thereafter, the aforementioned operations (1) to (3) are repeated in accordance with needs, whereby hydrogenation of phthalonitrile can be continuously performed for a long period of time.

(Method of Recovery of Xylylenediamine)

No particular limitation is imposed on the method of recovering xylylenediamine produced through hydrogenation of phthalonitrile, and a known method may be employed.

In one exemplary method, high-boiling-point by-products, high-boiling-point by-product precursors, low-boiling-point substances, etc., are removed, through distillation, from the hydrogenation reaction mixture which has passed through the reactor filled with a catalyst, whereby there can be yielded xylylenediamine having a purity, as determined through gas chromatography (hereinafter abbreviated as GC), of 99 mass % or higher. In the case of hydrogenation of isophthalonitrile, m-xylylenediamine having a GC purity of about 99.95 mass % can be generally yielded. m-Xylylenediamine can be also recovered, through distillation, from the washing liquid which has been use in the washing operation.

EXAMPLES

The present invention will next be described in more detail by way of examples, which should not be construed as limiting the invention thereto.

In the following Examples and Comparative Examples, m-xylylenediamine may be abbreviated as MXDA.

In the Examples and Comparative Examples, gas chromatographic (GC) analysis of hydrogenation reaction mixtures and measurement of the differential pressure of the catalyst layer were performed under the following conditions. The timing of gas chromatographic (GC) analysis after a sample was taken from hydrogenation reaction mixtures varies depending on each case.

[Gas Chromatographic Analysis (Qualitative and Quantitative Analyses)]
Apparatus: Agilent 6890 (product of Agilent Technologies)
Injection inlet temperature: 230° C.
Column: Agilent J&W GC Column "DB-1" (product of Agilent Technologies)

Column temperature: 100° C. to 280° C.
Detector: Flame ionization detector (FID)
Injection: A raw material or a liquid sample was diluted with methanol or tetrahydrofuran so that the amount of each ingredient other than the solvent was adjusted to 1 to 5 mass, and the thus-diluted sample was injected.

[Measurement of Differential Pressure of Catalyst Layer]

A digital-type pressure meter (pressure sensor, product of VALCOM) was installed at the inlet and outlet of the reactor. The difference in pressure measurement was employed as the differential pressure of the catalyst layer. The greater the measured pressure difference, the worse the liquid passage status.

Example 1

Hydrogenation

A nickel/diatomaceous earth (carrier) catalyst (nickel content: 50 mass %, columnar, diameter: 3 mmφ, height: 3 mm) (120 mL) was charged into a reactor (inner diameter: 25 mmφ) made of SUS. The catalyst was reduced under a flow of hydrogen at 200° C. for activation and then cooled. Hydrogen gas was fed with pressure into the reactor via pipes connected to the reactor to thereby maintain the inside of the reactor constantly at 8 MPa. The reactor was heated to thereby maintain the inside temperature at 70° C.

Hydrogen gas was supplied through the inlet of the reactor at a flow rate of 13 L/h. While the flow conditions of hydrogen gas were maintained, a raw-material mixture liquid prepared from raw-material isophthalonitrile (product of Mitsubishi Gas Co., Inc., produced through ammoxidation of m-xylene, purity: ≥4 mass %) (1 part by mass) and liquid ammonia (product of Mitsubishi Chemical Corp., purity: 99.9 mass %) (9 parts by mass) were supplied through the inlet of the reactor at 139 g/h. Continuous hydrogenation was started at an inside temperature of the reactor of 70° C. in the trickle-bed mode. The hydrogenation reaction mixture produced through hydrogenation was extracted through the outlet of the reactor. After start of reaction, the hydrogenation reaction mixture was sampled through the outlet of the reactor at appropriate timings, and the obtained liquid samples were analyzed through gas chromatography.

(Stopping Hydrogenation: Operation (1))

Three hundred hours after the start of hydrogenation, only the supply of the raw-material liquid was stopped.

(Washing of Catalyst: Operation (2))

The inside temperature of the reactor was maintained at 70° C. MXDA (product of Mitsubishi Gas Co., Inc., GC purity: 99.9 mass %, isophthalonitrile content: about 510 ppm by mass (below GC detection limit)) (800 g) serving as a washing liquid was supplied to the reactor through the inlet thereof at 139 g/h (washing time: about 6 hours, one-path flow mode).

In the washing liquid which had been used in the washing of the catalyst, a high-boiling-point by-product precursor which was thought to be derived from MXDA was detected through liquid chromatography.

(Resuming Hydrogenation: Operation (3))

After completion of washing, while the flow conditions of hydrogen gas were maintained, a raw-material mixture liquid prepared from raw-material isophthalonitrile (1 part by mass) and liquid ammonia (9 parts by mass) was supplied through the inlet of the reactor at 139 g/h. Continuous hydrogenation was resumed at an inside temperature of the reactor of 70° C.

After resuming hydrogenation, the hydrogenation reaction mixture was sampled through the outlet of the reactor at appropriate timings, and the obtained liquid samples were analyzed through gas chromatography.

Table 1 shows changes over time in selectivity to MXDA and to reaction intermediate CBA and differential pressure of the catalyst layer in the reactor.

Comparative Example 1

The procedure of Example 1 was repeated, except that no hydrogenation stopping (operation (1)) or (operation (2)) was performed and hydrogenation was continued, to thereby perform continuous hydrogenation. After start of reaction, the hydrogenation reaction mixture was sampled through the outlet of the reactor at appropriate timings, and the obtained liquid samples were analyzed through gas chromatography.

Six hundred hours after the start of reaction, the conversion of raw-material isophthalonitrile was 100 mass %, the selectivity to the target reaction product, MXDA, of 78.1 mass %, and the selectivity to reaction intermediate CBA was 18.1 mass %, indicating a drop in hydrogenation catalytic activity. The differential pressure of the catalyst layer increased to 0.14 MPa.

Table 1 shows changes over time in selectivity to MXDA and to reaction intermediate CBA and differential pressure of the catalyst layer in the reactor.

Comparative Example 2

The procedure of Example 1 was repeated, except that hydrogenation temperature was changed from 70° C. to 80° C., and that no hydrogenation stopping (operation (1)) or (operation (2)) was performed and hydrogenation was continued, to thereby perform continuous hydrogenation. After start of reaction, the hydrogenation reaction mixture was sampled through the outlet of the reactor at appropriate timings, and the obtained liquid samples were analyzed through gas chromatography.

Eight hundred hours after the start of reaction, the differential pressure of the catalyst layer increased to 0.29 MPa. Further, 850 hours after the start of reaction, difficulty was encountered in supplying of the raw material liquid. Thus, hydrogenation was halted.

Table 1 shows changes over time in selectivity to MXDA and to reaction intermediate CBA and differential pressure of the catalyst layer in the reactor.

Comparative Example 3

The experimental and analytical procedure of Example 1 was repeated, except that a mixture (800 g) of MXDA (product of Mitsubishi Gas Co., Inc., GC purity: 99.9 mass %, isophthalonitrile content: about 510 ppm by mass (below GC detection limit)) (768 g) and isophthalonitrile (32 g) was employed as a washing liquid (isophthalonitrile concentration: 4 mass %). Through liquid chromatography, a high-boiling-point by-product precursor conceivably originating from MXDA was detected in the washing liquid used in the washing operation.

Three hundred hours after the start of reaction, the conversion of raw-material isophthalonitrile was 100 mass %, the selectivity to the target reaction product, MXDA, of 77.3 mass %, and the selectivity to reaction intermediate CBA was 16.7 mass %, indicating a drop in hydrogenation catalytic activity. The differential pressure of the catalyst layer increased to 0.13 MPa.

Table 1 shows changes over time in selectivity to MXDA and to reaction intermediate CBA and differential pressure of the catalyst layer in the reactor.

Comparative Example 4

The experimental and analytical procedure of Example 1 was repeated, except that liquid ammonia was employed as a washing liquid. Through liquid chromatography, a high-boiling-point by-product precursor conceivably originating from MXDA was detected in the washing liquid used in the washing operation.

Three hundred hours after the start of reaction, the conversion of raw-material isophthalonitrile was 100 mass %, the selectivity to the target reaction product, MXDA, of 78.8 mass %, and the selectivity to reaction intermediate CBA was 17.3 mass %, indicating a drop in hydrogenation catalytic activity. The differential pressure of the catalyst layer increased to 0.12 MPa.

Table 1 shows changes over time in selectivity to MXDA and to reaction intermediate CBA and differential pressure of the catalyst layer in the reactor.

Example 2

The experimental and analytical procedure of Example 1 was repeated, except that a hydrogenation liquid [MXDA (GC purity: 94 mass %, isophthalonitrile content: about ≤10 ppm by mass (below GC detection limit))] from which liquid ammonia had been removed was employed as a washing liquid. Through liquid chromatography, a high-boiling-point by-product precursor conceivably originating from MXDA was detected in the washing liquid used in the washing operation.

Table 2 shows changes over time in selectivity to MXDA and to reaction intermediate CBA and differential pressure of the catalyst layer in the reactor.

Example 3

The experimental and analytical procedure of Example 1 was repeated, except that a mixture (800 g) of MXDA (product of Mitsubishi Gas Co., Inc., GC purity: 99.9 mass %, isophthalonitrile content: about 510 ppm by mass (below GC detection limit)) (128 g) and liquid ammonia (672 g) was employed as a washing liquid (MXDA concentration: 16 mass %). Through liquid chromatography, a high-boiling-point by-product precursor conceivably originating from MXDA was detected in the washing liquid used in the washing operation.

Table 2 shows changes over time in selectivity to MXDA and to reaction intermediate CBA and differential pressure of the catalyst layer in the reactor.

Example 4

The experimental and analytical procedure of Example 1 was repeated, except that a mixture (800 g) of MXDA (product of Mitsubishi Gas Co., Inc., GC purity: 99.9 mass %, isophthalonitrile content: about 510 ppm by mass (below GC detection limit)) (40 g) and liquid ammonia (760 g) was employed as a washing liquid (MXDA concentration: 5 mass %). Through liquid chromatography, a high-boiling-point by-product precursor conceivably originating from MXDA was detected in the washing liquid used in the washing operation.

Table 2 shows changes over time in selectivity to MXDA and to reaction intermediate CBA and differential pressure of the catalyst layer in the reactor.

Example 5

The experimental and analytical procedure of Example 1 was repeated, except that the first hydrogenation temperature and the hydrogenation temperature employed in the resuming of hydrogenation [operation (3)] were changed from 70° C. to 80° C., that only the supply of the raw material liquid was stopped 800 hours after the start of reaction in operation (1), and that the temperature of washing of the catalyst [operation (2)] was changed from 70° C. to 110° C. Through liquid chromatography, a high-boiling-point by-product precursor conceivably originating from MXDA was detected in the washing liquid used in the washing operation.

Table 2 shows changes over time in selectivity to MXDA and to reaction intermediate CBA and differential pressure of the catalyst layer in the reactor.

Example 6

The experimental and analytical procedure of Example 1 was repeated, except that the temperature of washing of the catalyst [operation (2)] was changed from 70° C. to 20° C. Through liquid chromatography, a high-boiling-point by-product precursor conceivably originating from MXDA was detected in the washing liquid used in the washing operation.

Table 2 shows changes over time in selectivity to MXDA and to reaction intermediate CBA and differential pressure of the catalyst layer in the reactor.

Example 7

Hydrogenation

The hydrogenation procedure of Example 1 was repeated, except that the hydrogenation temperature was changed from 70° C. to 80° C.

(Stopping Hydrogenation—1: Operation (1))

Hundred hours after the start of hydrogenation, only the supply of the raw-material liquid was stopped.

(Washing of Catalyst—1: Operation (2))

The inside temperature of the reactor was elevated from 80° C. to 90° C. MXDA (product of Mitsubishi Gas Co., Inc., GC purity: 99.9 mass %, isophthalonitrile content: about ≤10 ppm by mass (below GC detection limit)) (800 g) serving as a washing liquid was supplied to the reactor through the inlet thereof at 139 g/h. In the washing liquid used in the washing operation, a very small amount of a high-boiling-point by-product precursor conceivably originating from MXDA was detected through liquid chromatography.

(Resuming Hydrogenation—1: Operation (3))

After completion of washing, while the flow conditions of hydrogen gas were maintained, a raw-material mixture liquid prepared from raw-material isophthalonitrile (1 part by mass) and liquid ammonia (9 parts by mass) was supplied through the inlet of the reactor at 139 g/h. Continuous hydrogenation was resumed at an inside temperature of the reactor of 80° C.

(Stopping Hydrogenation—2: Operation (1))

Hundred hours after resuming of the hydrogenation, only the supply of the raw-material liquid was stopped again.

(Washing of Catalyst—2: Operation (2))

The inside temperature of the reactor was elevated from 80° C. to 90° C. MXDA (product of Mitsubishi Gas Co., Inc., GC purity: 99.9 mass %, isophthalonitrile content: about 510 ppm by mass (below GC detection limit)) (800 g) serving as a washing liquid was supplied to the reactor through the inlet thereof at 139 g/h. In the washing liquid used in the washing operation, a very small amount of a high-boiling-point by-product precursor conceivably originating from MXDA was detected through liquid chromatography.

(Resuming Hydrogenation—2: Operation (3))

After completion of washing, while the flow conditions of hydrogen gas were maintained, a raw-material mixture liquid prepared from raw-material isophthalonitrile (1 part by mass) and liquid ammonia (9 parts by mass) was supplied through the inlet of the reactor at 139 g/h. Continuous hydrogenation was resumed at an inside temperature of the reactor of 80° C.

Table 2 shows changes over time in selectivity to MXDA and to reaction intermediate CBA and differential pressure of the catalyst layer in the reactor.

TABLE 1

Example 1

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.2 | 0.01 | 0.01 |
| 100 | 95.3 | 0.06 | 0.01 |
| 150 | 95.0 | 0.4 | 0.02 |
| 200 | 94.5 | 1.8 | 0.02 |
| 250 | 92.9 | 3.1 | 0.03 |
| 300 | 90.2 | 6.9 | 0.03 |

- Operation (1) -
Halting hydrogenation
- Operation (2) -
Washing catalyst with MXDA (purity: ≥99.9%) (washing temp.: 70° C.)
- Operation (3) -
Resuming hydrogenation (70° C.)

| Point in Time after resuming reaction (hr) | MXDA (mass %) | Reaction intermediate CBA (mass %) | Differential pressure of catalyst layer (MPa) |
|---|---|---|---|
| 50 | 95.3 | 0.01 | 0.02 |
| 100 | 95.3 | 0.03 | 0.03 |
| 150 | 95.1 | 0.2 | 0.03 |
| 200 | 95.2 | 1.2 | 0.04 |
| 250 | 95.1 | 1.9 | 0.04 |
| 300 | 94.9 | 3.2 | 0.05 |

Comparative Example 1

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.0 | 0.01 | 0.01 |
| 100 | 95.2 | 0.05 | 0.01 |
| 150 | 94.9 | 0.3 | 0.02 |
| 200 | 94.6 | 2.0 | 0.02 |
| 250 | 92.5 | 3.2 | 0.03 |
| 300 | 90.1 | 7.3 | 0.03 |
| 400 | 86.6 | 11.5 | 0.05 |
| 500 | 83.4 | 13.7 | 0.08 |
| 600 | 78.1 | 18.1 | 0.14 |

Comparative Example 2

Hydrogenation (80° C.)

| Time of hydrogenation (hr) | MXDA (mass %) | Reaction intermediate CBA (mass %) | Differential pressure of catalyst layer (MPa) |
|---|---|---|---|
| 50 | 95.2 | 0.01 | 0.01 |
| 100 | 95.3 | 0.05 | 0.01 |
| 200 | 94.5 | 1.6 | 0.02 |
| 300 | 91.7 | 6.7 | 0.03 |
| 500 | 89.8 | 7.2 | 0.09 |
| 800 | 84.0 | 12.1 | 0.29 |

Comparative Example 3

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.2 | 0.01 | 0.01 |
| 100 | 94.9 | 0.08 | 0.01 |
| 150 | 94.7 | 0.6 | 0.02 |
| 200 | 94.0 | 2.4 | 0.02 |
| 250 | 91.8 | 3.8 | 0.03 |
| 300 | 89.4 | 7.9 | 0.03 |

- Operation (1) -
Halting hydrogenation
- Operation (2) -
Washing catalyst with reaction mixture (isophthalonitrile concentration: 4%, MXDA concentration: 96%) (washing temp.: 70° C.)
- Operation (3) -
Resuming hydrogenation (70° C.)

| Point in Time after resuming reaction (hr) | MXDA (mass %) | Reaction intermediate CBA (mass %) | Differential pressure of catalyst layer (MPa) |
|---|---|---|---|
| 50 | 90.6 | 5.8 | 0.04 |
| 100 | 88.3 | 6.9 | 0.05 |
| 150 | 85.9 | 8.2 | 0.06 |
| 200 | 83.9 | 9.4 | 0.08 |
| 250 | 81.9 | 12.5 | 0.10 |
| 300 | 77.3 | 16.7 | 0.13 |

Comparative Example 4

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.3 | 0.01 | 0.01 |
| 100 | 95.0 | 0.07 | 0.01 |
| 150 | 94.6 | 0.6 | 0.02 |
| 200 | 94.3 | 2.3 | 0.02 |

TABLE 1-continued

| | | | |
|---|---|---|---|
| 250 | 91.7 | 2.6 | 0.03 |
| 300 | 89.8 | 7.7 | 0.03 |

- Operation (1) -
Halting hydrogenation
- Operation (2) -
Washing catalyst with liquid ammonia 100% (washing temp.: 70° C.)
- Operation (3) -
Resuming hydrogenation (70° C.)

| Point in Time after resuming reaction (hr) | MXDA (mass %) | Reaction intermediate CBA (mass %) | Differential pressure of catalyst layer (MPa) |
|---|---|---|---|
| 50 | 89.7 | 7.6 | 0.03 |
| 100 | 87.5 | 8.3 | 0.04 |
| 150 | 84.8 | 9.0 | 0.05 |
| 200 | 85.6 | 12.1 | 0.07 |
| 250 | 83.9 | 13.7 | 0.19 |
| 300 | 78.8 | 17.3 | 0.12 |

TABLE 2

Example 2

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.1 | 0.01 | 0.01 |
| 100 | 95.2 | 0.06 | 0.01 |
| 150 | 94.9 | 0.5 | 0.02 |
| 200 | 94.5 | 1.8 | 0.02 |
| 250 | 92.7 | 3.3 | 0.03 |
| 300 | 90.0 | 6.8 | 0.03 |

- Operation (1) -
Halting hydrogenation
- Operation (2) -
Washing catalyst with reaction mixture (MXDA concentration: 94%) (washing temp.: 70° C.)
- Operation (3) -
Resuming hydrogenation (70° C.)

| Point in Time after resuming reaction (hr) | MXDA (mass %) | Reaction intermediate CBA (mass %) | Differential pressure of catalyst layer (MPa) |
|---|---|---|---|
| 50 | 95.0 | 0.01 | 0.02 |
| 100 | 95.0 | 0.08 | 0.03 |
| 150 | 95.3 | 0.5 | 0.03 |
| 200 | 95.1 | 1.8 | 0.04 |
| 250 | 94.7 | 2.6 | 0.04 |
| 300 | 94.2 | 4.3 | 0.05 |

Example 3

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.2 | 0.01 | 0.01 |
| 100 | 95.1 | 0.05 | 0.01 |
| 150 | 94.9 | 0.4 | 0.02 |
| 200 | 94.2 | 1.9 | 0.02 |

TABLE 2-continued

| | | | |
|---|---|---|---|
| 250 | 92.3 | 3.2 | 0.03 |
| 300 | 89.9 | 7.0 | 0.03 |

- Operation (1) -
Halting hydrogenation
- Operation (2) -
Washing catalyst with liquid ammonia mixture (MXDA concentration: 16%) (washing temp.: 70° C.)
- Operation (3) -
Resuming hydrogenation (70° C.)

| Point in Time after resuming reaction (hr) | MXDA (mass %) | Reaction intermediate CBA (mass %) | Differential pressure of catalyst layer (MPa) |
|---|---|---|---|
| 50 | 94.7 | 4.1 | 0.03 |
| 100 | 93.6 | 5.4 | 0.03 |
| 150 | 92.2 | 6.3 | 0.04 |
| 200 | 91.0 | 7.2 | 0.04 |
| 250 | 89.9 | 9.3 | 0.05 |
| 300 | 86.8 | 11.7 | 0.06 |

Example 4

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.0 | 0.01 | 0.01 |
| 100 | 94.8 | 0.09 | 0.01 |
| 150 | 95.0 | 0.5 | 0.02 |
| 200 | 94.1 | 2.2 | 0.02 |
| 250 | 92.1 | 3.6 | 0.03 |
| 300 | 89.7 | 7.6 | 0.03 |

- Operation (1) -
Halting hydrogenation
- Operation (2) -
Washing catalyst with liquid ammonia mixture (MXDA concentration: 5%) (washing temp.: 70° C.)
- Operation (3) -
Resuming hydrogenation (70° C.)

| Point in Time after resuming reaction (hr) | MXDA (mass %) | Reaction intermediate CBA (mass %) | Differential pressure of catalyst layer (MPa) |
|---|---|---|---|
| 50 | 93.1 | 5.2 | 0.03 |
| 100 | 91.5 | 6.1 | 0.04 |
| 150 | 89.2 | 7.5 | 0.05 |
| 200 | 88.0 | 8.9 | 0.06 |
| 250 | 85.6 | 11.9 | 0.08 |
| 300 | 80.8 | 15.0 | 0.10 |

Example 5

Hydrogenation (80° C.)

| Time of hydrogenation (hr) | MXDA (mass %) | Reaction intermediate CBA (mass %) | Differential pressure of catalyst layer (MPa) |
|---|---|---|---|
| 50 | 95.4 | 0.01 | 0.01 |
| 100 | 95.0 | 0.05 | 0.01 |
| (200) | 94.3 | 1.6 | 0.02 |
| (300) | 92.1 | 6.7 | 0.03 |

TABLE 2-continued

| | | | |
|---|---|---|---|
| (500) | 88.6 | 7.2 | 0.09 |
| (800) | 82.5 | 13.9 | 0.29 |

- Operation (1) -
Halting hydrogenation
- Operation (2) -
Washing catalyst with MXDA (purity: ≥99.9%)
(washing temp.: 110° C.)
- Operation (3) -
Resuming hydrogenation (80° C.)

| Point in Time after resuming reaction (hr) | MXDA (mass %) | Reaction intermediate CBA (mass %) | Differential pressure of catalyst layer (MPa) |
|---|---|---|---|
| 0 | — | — | 0.02 |
| 50 | 95.3 | 0.02 | 0.03 |
| 100 | 95.3 | 0.05 | 0.03 |
| 150 | 95.1 | 0.2 | 0.04 |
| 200 | 95.2 | 1.2 | 0.04 |
| 250 | 94.9 | 2.3 | 0.05 |
| 300 | 93.2 | 3.7 | 0.06 |

Example 6

Hydrogenation (70° C.)

| Time of hydrogenation (hr) | MXDA (mass %) | Reaction intermediate CBA (mass %) | Differential pressure of catalyst layer (MPa) |
|---|---|---|---|
| 50 | 95.1 | 0.01 | 0.01 |
| 100 | 94.9 | 0.07 | 0.01 |
| 150 | 94.7 | 0.6 | 0.02 |
| 200 | 93.9 | 2.5 | 0.02 |
| 250 | 91.8 | 2.8 | 0.03 |
| 300 | 89.9 | 7.2 | 0.03 |

- Operation (1) -
Halting hydrogenation
- Operation (2) -
Washing catalyst with MXDA (purity: ≥99.9%)
(washing temp.: 20° C.)
- Operation (3) -
Resuming hydrogenation (70° C.)

| Point in Time after resuming reaction (hr) | MXDA (mass %) | Reaction intermediate CBA (mass %) | Differential pressure of catalyst layer (MPa) |
|---|---|---|---|
| 50 | 90.3 | 6.7 | 0.03 |
| 100 | 89.8 | 7.2 | 0.03 |
| 150 | 88.0 | 8.5 | 0.04 |
| 200 | 86.8 | 10.6 | 0.05 |
| 250 | 85.9 | 12.0 | 0.07 |
| 300 | 83.2 | 14.5 | 0.09 |

Example 7

Hydrogenation (80° C.)

| Time of hydrogenation (hr) | MXDA (mass %) | Reaction intermediate CBA (mass %) | Differential pressure of catalyst layer (MPa) |
|---|---|---|---|
| 50 | 95.2 | 0.01 | 0.01 |
| 100 | 95.3 | 0.04 | 0.01 |

- Operation (1) -
1st Halting hydrogenation
- Operation (2) -
Washing catalyst with MXDA (purity: ≥99.9%)
(washing temp.: 90° C.)
- Operation (3) -
Resuming hydrogenation (80° C.)

| Point in Time after resuming reaction (hr) | MXDA (mass %) | Reaction intermediate CBA (mass %) | Differential pressure of catalyst layer (MPa) |
|---|---|---|---|
| 0 | | | 0.01 |
| 50 | 95.4 | 0.01 | 0.01 |
| 100 | 95.2 | 0.05 | 0.01 |

- Operation (1) -
2nd Halting hydrogenation
- Operation (2) -
Washing catalyst with MXDA (purity: ≥99.9%)
(washing temp.: 90° C.)
- Operation (3) -
Resuming hydrogenation (80° C.)

| Point in Time after resuming reaction (hr) | MXDA (mass %) | Reaction intermediate CBA (mass %) | Differential pressure of catalyst layer (MPa) |
|---|---|---|---|
| 0 | | | 0.01 |
| 50 | 95.3 | 0.01 | 0.01 |
| 100 | 95.2 | 0.04 | 0.01 |

In Examples 1 to 7, the reaction intermediate CBA level and the differential pressure of the catalyst layer were measured immediately after resuming the hydrogenation or 50 hours after resuming the hydrogenation. As a result, effects of regenerating and activating the catalyst and an effect of improving the differential pressure of the catalyst layer were confirmed.

In contrast, in Comparative Examples 1 and 2 in which washing of the catalyst was not performed, the reaction intermediate CBA level and the differential pressure of the catalyst layer continuously increased. Particularly, in Comparative Example 2 in which the reaction was performed for a long period of time, supply of raw materials was impeded, to thereby stop continuous hydrogenation. Thus, the processes of Comparative Examples 1 and 2 were found to be not suitable for industrial long-term production.

Even though washing of the catalyst was performed, when the employed washing liquid had an isophthalonitrile concentration higher than 3 mass % (Comparative Example 3) or an MXDA concentration less than 1 mass % (Comparative Example 4), satisfactory effects of regenerating and activating the catalyst failed to be attained. Also, the effect of improving the differential pressure of the catalyst layer was unsatisfactory. Thus, the processes of Comparative Examples 3 and 4 encountered difficulty in industrially performing them. Notably, the analysis performed in Comparative Example 3 was indicated that when the hydrogenation reaction mixture obtained in hydrogenation was employed as a washing liquid, the isophthalonitrile concentration of the hydrogenation reaction mixture must be reduced to 3 mass % or less before use.

When the results of Example 1 obtained 300 hours after resuming hydrogenation are compared with the results of Comparative Examples 1 to 4 obtained 600 hours after the start of hydrogenation, remarkably excellent effects of the present invention can be confirmed.

INDUSTRIAL APPLICABILITY

The xylylenediamine produced through the production process of the present invention is a useful starting substance for synthesizing, for example, polyamide and epoxy curing agents, or a useful intermediate in production of isocyanate resin.

The invention claimed is:

1. A process for producing a xylylenediamine by supplying a solution of phthalonitrile dissolved in a solvent to a reactor filled with a catalyst and hydrogenating the phthalonitrile to produce xylylenediamine, the process comprising:
   (1) halting supply of the solution;
   (2) bringing a washing liquid into contact with the catalyst, the washing liquid having a phthalonitrile content of 3 mass % or less and a xylylenediamine content of 5 mass % or more to at least partially regenerate the catalyst; and
   (3) after completion of the contact, resuming supply of the solution, and employing the catalyst continuously in hydrogenation.

2. The process for producing a xylylenediamine according to claim 1, wherein the washing liquid is brought into contact with the catalyst at 20 to 180° C.

3. The process for producing a xylylenediamine according to claim 1, wherein at least a portion of the washing liquid is brought into contact with the catalyst in a circulation flow mode or a one-path flow mode.

4. The process for producing a xylylenediamine according to claim 1, wherein the washing liquid is brought into contact with the catalyst under a hydrogen atmosphere.

5. The process for producing a xylylenediamine according to claim 1, wherein the phthalonitrile is an isophthalonitrile.

6. The process for producing a xylylenediamine according to claim 1, wherein the solvent is a liquid ammonia.

7. The process for producing a xylylenediamine according to claim 1, wherein the washing liquid is brought into contact with the catalyst under a nitrogen atmosphere.

8. The process for producing a xylylenediamine according to claim 1,
   wherein the washing liquid is a hydrogenation reaction mixture obtained through hydrogenation of a phthalonitrile.

9. The process for producing a xylylenediamine according to claim 8, wherein
   the solvent is a liquid ammonia, and
   a hydrogenation reaction mixture from which a portion or the entirety of the liquid ammonia has been removed is the washing liquid.

10. The process for producing a xylylenediamine according to claim 1,
   wherein the xylylenediamine produced is m-xylylenediamine, and wherein the washing liquid comprises m-xylylenediamine.

11. The process for producing a xylylenediamine according to claim 1,
   wherein the xylylenediamine content of the washing liquid is 5 to 100 mass %.

12. The process for producing a xylylenediamine according to claim 1,
   wherein the xylylenediamine content of the washing liquid is 10 to 100 mass %.

13. The process for producing a xylylenediamine according to claim 1,
   wherein the xylylenediamine content of the washing liquid is 50 to 100 mass %.

14. The process for producing a xylylenediamine according to claim 1,
   wherein the xylylenediamine content of the washing liquid is 95 to 100 mass %.

15. The process for producing a xylylenediamine according to claim 1,
   wherein the xylylenediamine content of the washing liquid is 99 to 100 mass %.

16. A process for producing a xylylenediamine by supplying a solution of phthalonitrile dissolved in a solvent to a reactor filled with a catalyst and hydrogenating the phthalonitrile to produce xylylenediamine, the process comprising:
   (1) halting supply of the solution;
   (2) bringing a washing liquid into contact with the catalyst, the washing liquid having a phthalonitrile content of 3 mass % or less and a xylylenediamine content of 1 mass % or more; and
   (3) after completion of the contact, resuming supply of the solution, and employing the catalyst continuously in hydrogenation,
   wherein the washing liquid is a hydrogenation reaction mixture obtained through hydrogenation of a phthalonitrile.

17. The process for producing a xylylenediamine according to claim 16, wherein
   the solvent is a liquid ammonia, and
   a hydrogenation reaction mixture from which a portion or the entirety of the liquid ammonia has been removed is the washing liquid.

* * * * *